United States Patent [19]

Kurihara et al.

[11] Patent Number: 5,210,097
[45] Date of Patent: May 11, 1993

[54] XANTHOCILLIN X MONOMETHYL ETHER DERIVATIVE AND ANTITUMOR AGENT CONTAINING THE SAME

[75] Inventors: Hiroshi Kurihara; Hiromi Watanabe; Masao Koyama; Masaji Sezaki; Tsutomu Tsuruoka; Harumi Fukuyasu; Haruo Yamamoto, all of Kanagawa, Japan

[73] Assignee: Meiji Seika Kaisha Ltd., Tokyo, Japan

[21] Appl. No.: 524,954

[22] Filed: May 18, 1990

[30] Foreign Application Priority Data

May 18, 1989 [JP] Japan .................................. 1-122991

[51] Int. Cl.$^5$ .................... A61K 31/275; C07C 265/06
[52] U.S. Cl. ........................................ 514/525; 558/302
[58] Field of Search .......................... 558/302; 514/525

[56] References Cited

PUBLICATIONS

Devita et al. Cancer, Principles and Practice of Oncology 144–145.
Riggs Principles of Cancer Chemotherapy.
The Journal of Antibiotics, vol. 34, No. 12, Dec. 1981, pp. 1556–1661.
The Journal of Antibiotics, vol. 21, No. 10, Oct. 1968, pp. 582–586.
Chemical Abstracts, vol. 68, No. 13, Abstract 57611h, p. 5562, Mar. 25, 1968, (Hans).
Takatsuki et al CA 70-56257b.

Primary Examiner—Jane T. Fan
Attorney, Agent, or Firm—Sughrue, Mion, Zinn, Macpeak & Seas

[57] ABSTRACT

A xanthocillin X monomethyl ether derivative represented by the formula (I)

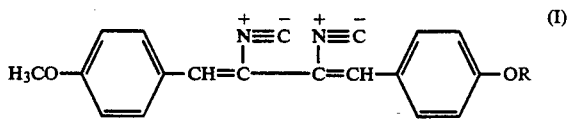

wherein R represents an alkyl group, an alkenyl group, an alkoxycarbonyl group, an aralkyl group, an alkyl group substituted with a pyridyl group or a halogen atom, an aralkyl group substituted with an alkyl group or a halogen atom, or an aroyl group, which exerts an intense effect of inhibiting the proliferation of a tumor, in particular, a solid tumor.

3 Claims, No Drawings

XANTHOCILLIN X MONOMETHYL ETHER DERIVATIVE AND ANTITUMOR AGENT CONTAINING THE SAME

FIELD OF THE INVENTION

This invention relates to a xanthocillin X monomethyl ether derivative and an antitumor agent containing the same as an active ingredient.

BACKGROUND OF THE INVENTION

Malignant tumors rank first among death causes in Japan. Thus various treatments including chemotherapeutic, surgical and radiotherapeutic ones have been remarkably advanced in order to overcome this disease. Recently progress in chemotherapy has made it possible to overcome specific cancers such as juvenile leukemia little by little. In the case of solid tumors, however, surgical treatments are still mainly effected and there are few cases where this disease is healed exclusively by chemotherapy only. Many chemotherapeutic agents would exert only limited growth suppressing effects on solid tumors. Furthermore, various side effects accompanying chemotherapy substantially restrict these treatments.

Xanthocillin X monomethyl ether, which is the starting material for the synthesis of the compound of the present invention, is a known substance produced by *Dichotomomyces albus* belonging to Fungi Imperfecti (cf. K. Ando et al., J. Antibiotics, 21, 582–586 (1968)). Xanthocillin X monomethyl ether was purified and isolated as an antiviral substance. Furthermore, studies on the antitumor activity of this compound revealed that it would suppress the proliferation of Ehrich ascites tumor but the cancer cells would proliferate again immediately after stopping the administration of this compound. These results suggested that xanthocillin X monomethyl ether was not practically available as an antitumor agent. Individually, it was clarified that this compound would inhibit the biosynthesis of prostaglandin or thromboxane, namely, the conversion of arachidonic acid into prostaglandin $H_2$ (cf. N. Kitahara et al., J. Antibiotics, 34, 1556–1561 (1981)).

SUMMARY OF THE INVENTION

An object of the present invention is to provide xanthocillin X monomethyl ether derivatives having an antitumor activity.

Another object of the present invention is to provide an antitumor agent containing the xanthocillin X monomethyl ether derivative.

We attempted to chemically modify xanthocillin X monomethyl ether and consequently, have succeeded in the production of derivatives which show therapeutic effects on many kinds of cancer, in particular, solid tumors and has a low toxicity.

Thus, the present invention relates to a xanthocillin monomethyl ether derivative, i.e., 1-(4'-hydroxyphenyl)-2,3-diisocyano-4-(4'-methoxyphenyl)-1,3-butadiene derivative, represented by the following general formula (I):

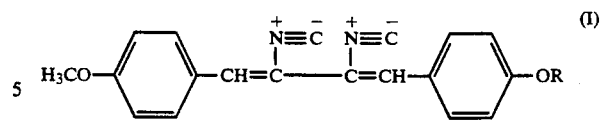

wherein R represents an alkyl group, an alkenyl group, an alkoxycarbonyl group, an aralkyl group, an alkyl group substituted with a pyridyl group or a halogen atom, an aralkyl group substituted with an alkyl group or a halogen atom, or an aroyl group and to an antitumor agent containing an antitumor effective amount of the derivative as an active ingredient and a pharmaceutically acceptable carrier.

DETAILED DESCRIPTION OF THE INVENTION

The compound of the present invention is highly effective in the treatment of a number of tumors, in particular, solid tumors. Examples of the xanthocillin X monomethyl ether derivative, namely, the active ingredient of the present invention are as follows, though the present invention is not restricted thereby:

Compound No. 1: 1-(4'-ethoxycarbonyloxyphenyl)-4-(4'-methoxyphenyl)-2,3-diisocyano-1,3-butadiene, Compound No. 2: 1-(4'-benzyloxyphenyl)-4-(4'-methoxyphenyl)- 2,3-diisocyano-1,3-butadiene, Compound No. 3: 1-[4'-(2''-fluoroethyl)oxyphenyl]-4-(4'-methoxyphenyl)-2,3-diisocyano-1,3-butadiene, Compound No. 4: 1-(4'-n-hexyloxyphenyl)-4-(4'-methoxyphenyl)-2,3-diisocyano-1,3-butadiene, Compound No. 5: 1-[4'-(4''-pyridyl)methyloxyphenyl]-4-(4'-methoxyphenyl)-2,3-diisocyano-1,3-butadiene, Compound No. 6: 1-[4'-(2''-pyridyl)methyloxyphenyl]-4-(4'-methoxyphenyl)-2,3-diisocyano-1,3-butadiene, Compound No. 7: 1-[4'-(4''-toluyl)methyloxyphenyl]-4-(4'-methoxyphenyl)-2,3-diisocyano-1,3-butadiene, Compound No. 8: 1-(4'-benzoyloxyphenyl)-4-(4'-methoxy phenyl)-2,3-diisocyano-1,3-butadiene, Compound No. 9: 1-[4'-(4''-chlorophenyl)methyloxyphenyl]-4-(4'-methoxy-phenyl)-2,3-diisocyano-1,3-butadiene, and Compound No. 10: 1-[4'-(2''-propenyl)oxyphenyl]-4-(4'-methoxyphenyl)-2,3-di-isocyano-1,3-butadiene.

The xanthocillin X monomethyl ether of the present invention may be synthesized by a common method shown by the following reaction scheme:

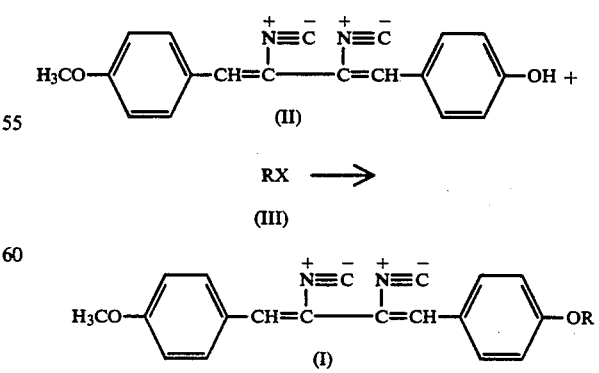

wherein R is as defined above; and X represents a halogen atom. X preferably represents a chlorine atom, a bromine atom and an iodine atom.

This process comprises dissolving xanthocillin X monomethyl ether (II) and a halogen derivative (III) in an appropriate organic solvent (for example, dimethylformamide, methylene chloride, acetone), adding an appropriate base (for example, potassium carbonate, triethylamine) thereto, stirring the obtained mixture at room temperature for 30 minutes to 48 hours, pouring the reaction mixture into water, extracting the same with an appropriate organic solvent (for example, ethyl acetate, chloroform) and distilling off the solvent to thereby give the compounds of the present invention of the general formula (I). These compounds may be further purified by a conventional method such as recrystallization or column chromatography, if required.

The compound of the present invention may be used alone as an antitumor agent or formulated into various preparations together with pharmaceutically acceptable carriers. Furthermore, it may be used in combination with known antitumor antibiotics, antitumor immunity substances and antimetabolites. It may be either orally or parenterally administered to mammals for therapeutic purposes.

In the case of parenteral administration, the compound may be formulated into, for example, intravenous, subcutaneous or intramuscular injection, or suppository. Alternately, it may be directly applied to a tumor so as to achieve an enhanced effect.

Examples of a parenteral preparation include aseptic aqueous or nonaqueous solutions and emulsions. These nonaqueous solutions or emulsions contain a base (for example, propylene glycol, polyethylene glycol, glycerol, olive oil, corn oil, ethyl oleate). On the other hand, the suppositories may contain a base (for example, cacao fat, macrogol).

In the case of oral administration, the compound of the present invention may be formulated into, for example, capsule, tablet, granules, fine subtilaes and dust by a conventional method. These oral preparations may contain fillers (for example, starch, lactose, mannitol, ethyl cellulose, sodium carboxymethyl cellulose), lubricants (for example, magnesium stearate, calcium stearate) and binders (for example, gelatin, gum arabic, cellulose ester, polyvinyl pyrrolidone).

The compound according to the present invention may be administered to an adult in a dose of from 100 to 3000 mg once or several times per day. The dose should be appropriately determined depending on the age, body weight and symptom of the patient as well as the route and frequency of the administration.

The compound of the present invention shows a low toxicity and an extremely intense effect of inhibiting the proliferation of tumor cells on which known drugs are scarcely effective. Thus the present invention provides a novel and effective antitumor agent.

To further illustrate the present invention, and not by way of limitation, the following examples will be given.

EXAMPLE 1

Production of 1-(4'-ethoxycarbonyloxyphenyl)-4-(4'-methoxyphenyl)-2,3-diisocyano-1,3-butadiene (Compound No. 1)

96 mg of xanthocillin X monomethyl ether was dissolved in 3 ml of dimethylformamide (DMF) and 220 mg of potassium carbonate was added thereto. Further, 110 μl of ethyl bromoacetate was added thereto and the mixture thus formed was stirred at room temperature for 20 hours. Then the reaction mixture was poured into 50 ml of water and extracted with 30 ml portions of ethyl acetate thrice. The extracts were combined, successively washed with water and a saturated aqueous solution of sodium chloride and dried over sodium sulfate. The sodium sulfate was filtered off and the solvent was distilled from the filtrate. Thus 128 mg of a yellow solid substance was obtained. This product was applied on a silica gel column and elution was carried out with a mixture of ethyl acetate and hexane (1:10 by volume). The fraction containing the desired compound which were determined by thin-layer chromatography were combined. The resulting fraction was concentrated to give 99 mg of 1-(4'-ethoxycarbonyloxy-phenyl)-4-(4'-methoxyphenyl)-2,3-diisocyano-1,3-butadiene in the form of a yellow powdery solid. Yield: 79%.

NMR δ (CDCl$_3$): 1.30 (3H, t), 3.85 (2H, s), 4.25 (2H, q), 4.70 (3H, s), 7.05 (6H, m) and 7.80 (4H, d).

Mass M/Z: 388.

EXAMPLE 2

Production of 1-(4'-benzyloxyphenyl)-4-(4'-methoxyphenyl)-2,3-diisocyano-1,3-butadiene (Compound No. 2)

16 mg of xanthocillin X monomethyl ether was dissolved in 3 ml of DMF and 48 mg of potassium carbonate was added thereto. Further, 48 μl of benzyl bromide was added thereto and the mixture thus formed was stirred at room temperature for 20 hours. Then the reaction mixture was poured into 50 ml of water and extracted with 30 ml portions of ethyl acetate thrice. The extracts were combined, successively washed with water and a saturated aqueous solution of sodium chloride and dried over sodium sulfate. The sodium sulfate was filtered off and the solvent was distilled from the filtrate. Thus 20 mg of 1-(4'-benzyloxy- (5H, m) and 7.80 (4H, d).

Mass M/Z: 392.

EXAMPLE 3

Production of 1-[4'-(2''-fluoroethyl)oxyphenyl]-4-(4'-methoxyphenyl)-2,3-diiso-cyano-1,3-butadiene (Compound No. 3)

18 mg of xanthocillin X monomethyl ether was dissolved in 3 ml of DMF and 42 mg of potassium carbonate was added thereto. Further, 20 μl of 1-bromo-2-fluoroethane was added thereto and the mixture thus formed was stirred at room temperature for 20 hours. Then the reaction mixture was poured into 50 ml of water and extracted with 30 ml portions of ethyl acetate thrice. The extracts were combined, successively washed with water and a saturated aqueous solution of sodium chloride and dried over sodium sulfate. The sodium sulfate was filtered off to thereby give 20 mg of 1-[4'-(2''-fluoroethyl)oxyphenyl]-4-(4'-methoxyphenyl-2,3-diisocyano-1,3-butadiene in the form of a yellow solid. Yield: 95%.

NMR δ (CDCl$_3$): 3.85 (3H, s), 4.30 (2H, dd), 4.80 (2H, dd), 7.05 (6H, m) and 7.80 (4H, m).

Mass M/Z: 348.

EXAMPLE 4

Production of 1-(4'-n-hexyloxyphenyl)-4-(4'-methoxyphenyl)-2,3-diisocyano-1,3-butadiene (Compound No. 4)

13 mg of xanthocillin X monomethyl ether was dissolved in 2 ml of DMF and 40 mg of potassium carbonate was added thereto. Further, 50 μl of n-hexyl bromide was added thereto and the mixture thus formed was extracted with 30 ml portions of ethyl acetate thrice. The extracts were combined, successively washed with water and a saturated aqueous solution of sodium chloride and dried over sodium sulfate. The sodium sulfate was filtered off and the solvent was distilled from the filtrate. Thus 15 mg of 1-(4'-n-hexyloxyphenyl)-4-(4'-methoxyphenyl)-2,3-diisocyano-1,3-butadiene was obtained in the form of a brown solid. Yield: 94%.

NMR δ (CDCl$_3$): 1.90 (3H, t), 1.35 (4H, m), 1.50 (2H, t), 1.80 (2H, q), 3.90 (3H, s), 4.00 (2H, t), 7.00 (6H, m) and 7.80 (4H, q).

Mass M/Z: 386.

EXAMPLE 5

Production of
1-[4'-(4''-pyridyl)methoxyphenyl]-4-(4'-methoxyphenyl)-2,3-diisocyano-1,3-butadiene (Compound No. 5)

42 mg of xanthocillin X monomethyl ether was dissolved in 3 ml of DMF and 217 mg of potassium carbonate was added thereto. Further, 71 mg of 4-picolyl chloride was added thereto and the mixture thus formed was stirred at room temperature for 20 hours. Then the reaction mixture was poured into 50 ml of water and extracted with 30 ml portions of ethyl acetate thrice. The extracts were combined, successively washed with water and a saturated aqueous solution of sodium chloride and dried over sodium sulfate. The sodium sulfate was filtered off and the solvent was distilled from the filtrate. Thus 53 mg of a brown solid product was obtained. This product was purified by silica gel column chromatography in the same manner as in Example 1 to thereby give 33 mg of 1-[4'-(4''-pyridyl)-methoxyphenyl]-4-(4'-methoxyphenyl)-2,3-diisocyano-1,3-butadiene in the form of a yellow solid. Yield: 60%.

NMR δ (CDCl$_3$): 3.90 (3H, s), 5.15 (2H, s), 7.00 (6H, m), 7.35 (2H, d). 7.80 (4H, d) and 8.65 (2H, d).

Mass M/Z: 393.

EXAMPLE 6

Production of
1-[4'-(2''-pyridyl)methoxyphenyl]-4-(4'-methoxyphenyl)-2,3-diisocyano-1,3-butadiene (Compound No. 6)

47 mg of xanthocillin X monomethyl ether was dissolved in 5 ml of DMF and 215 mg of potassium carbonate was added thereto. Further, 65 mg of 2-picolyl chloride was added thereto and the mixture thus formed was stirred at room temperature for 20 hours. Then the reaction mixture was poured into 50 ml of water and extracted with 30 ml portions of ethyl acetate thrice. The extracts were combined, successively washed with water and a saturated aqueous solution of sodium chloride and dried over sodium sulfate. The sodium sulfate was filtered off and the solvent was distilled from the filtrate. Thus 52 mg of a yellow solid product was obtained. This product was purified by silica gel column chromatography in the same manner as in Example 1 to thereby give 28 mg of 1-[4'-(2''-pyridyl)methoxyphenyl]-4-(4'-methoxyphenyl)-2,3-diisocyano-1,3-butadiene in the form of a yellow solid. Yield: 85%.

NMR δ (CDCl$_3$): 3.90 (3H, s), 5.30 (2H, s), 7.00 (2H, d), 7.01 (1H, s), 7.03 (1H, s), 7.08 (2H, d), 7.25 (1H, t), 7.53 (1H, d), 7.75 (1H, t), 7.80 (4H, d) and 8.63 (1H, d).

Mass M/Z: 393.

EXAMPLE 7

Production of
1-[4'-(4''-toluyl)methoxyphenyl]-4-(4'-methoxyphenyl)-2,3-diisocyano-1,3-butadiene (Compound No. 7)

75 mg of xanthocillin X monomethyl ether was dissolved in 5 ml of DMF and 190 mg of potassium carbonate was added thereto. Further, 100 μl of α-chloro-p-xylene was added thereto and the mixture thus formed was stirred at room temperature for 20 hours. Then the reaction mixture was poured into 50 ml of water and extracted with 30 ml portions of ethyl acetate thrice. The extracts were combined, successively washed with water and a saturated aqueous solution of common salt and dried over sodium sulfate. The sodium sulfate was filtered and the solvent was distilled from the filtrate. Thus 368 mg of a yellow solid product was obtained. This product was purified by silica gel column chromatography in the same manner as in Example 1 to thereby give 82 mg of 1-[4'-(4''-toluyl)methoxyphenyl]-4-(4'-methoxyphenyl)-2,3-diisocyano-1,3-butadiene in the form of a yellow solid. Yield: 81%.

NMR δ (CDCl$_3$): 2.35 (3H, s), 3.90 (3H, s), 5.30 (2H, s), 7.00 (2H, m), 7.20 (2H, d), 7.35 (2H, d) and 7.80 (4H, q).

Mass M/Z: 406.

EXAMPLE 8

Production of
1-(4'-benzoyloxyphenyl)-4-(4'-methoxyphenyl)-2,3-diisocyano-1,3-butadiene (Compound No. 8)

76 mg of xanthocillin X monomethyl ether was dissolved in 5 ml of DMF and 170 mg of potassium carbonate was added thereto. Further, 35 μl of benzoyl chloride was added thereto and the mixture thus formed was stirred at room temperature for 20 hours. Then the reaction mixture was poured into 50 ml of water and extracted with 30 ml portions of chloroform thrice. The extracts were combined, successively washed with water and a saturated aqueous solution of sodium chloride and dried over magnesium sulfate. The magnesium sulfate was filtered off and the solvent was distilled from the filtrate. Thus 440 mg of a yellow solid product was obtained. This product was recrystallized from ethyl acetate to thereby give 97 mg of 1-(4'-benzoyloxyphenyl)-4-(4'-methoxyphenyl)-2,3-diisocyano-1,3-butadiene in the form of a yellow solid. Yield: 95%.

NMR δ (CDCl$_3$): 3.90 (3H, s), 7.00 (2H, d), 7.10 (2H, s), 7.35 (2H, d), 7.55 (2H, t), 7.65 (1H, t), 7.80 (2H, d), 7.90 (2H, d) and 8.20 (2H, d).

Mass M/Z: 406.

EXAMPLE 9

Production of
1-[4'-(4'''-chlorophenyl)methoxyphenyl]-4-(4'-methoxyphenyl)-2,3-diisocyano-1,3-butadiene (Compound No. 9)

77 mg of xanthocillin X monomethyl ether was dissolved in 5 ml of DMF and 171 mg of potassium carbonate was added thereto. Further, 90 μl of p-chlorobenzyl chloride was added thereto and the mixture thus formed was stirred at room temperature for 20 hours. Then the reaction mixture was poured into 50 ml of water and extracted with 30 ml portions of ethyl acetate thrice. The extracts were combined, successively washed with water and a saturated aqueous solution of sodium chloride and dried over magnesium sulfate. The magnesium sulfate was filtered off and the solvent was distilled from the filtrate. Thus 246 mg of a yellow solid product was obtained. This product was purified by silica gel column chromatography in the same manner as in Example 1 to thereby give 79 mg of 1-[4'-(4''-chlorophenyl)methoxyphenyl]-4-(4'-methoxyphenyl)-2,3-diisocyano-1,3-butadiene in the form of a yellow solid. Yield: 73%.

NMR δ (CDCl₃): 3.95 (3H, s), 5.10 (2H, s), 7.00 (6H, m), 7.35 (4H, s) and 7.80 (4H, t).

Mass M/Z: 426.

EXAMPLE 10

Production of 1-[4'-(2''-propenyl)oxyphenyl]-4-(4'-methoxyphenyl)-2,3-diisocyano-1,3-butadiene (Compound No. 10)

78 mg of xanthocillin X monomethyl ether was dissolved in 5 ml of DMF and 172 mg of potassium carbonate was added thereto. Further, 110 μl of allyl bromide was added thereto and the mixture thus formed was stirred at room temperature for 20 hours. Then the reaction mixture was poured into 50 ml of water and extracted with 30 ml portions of ethyl acetate thrice. The extracts were combined, successively washed with water and a saturated aqueous solution of sodium chloride and dried over magnesium sulfate. The magnesium sulfate was filtered off and the solvent was distilled from the filtrate. Thus 225 mg of a yellow solid product was obtained. This product was purified by silica gel column chromatography in the same manner as in Example 1 to thereby give 48 mg of 1-[4'-(2''-propenyl)oxyphenyl]-4-(4'-methoxyphenyl)-2,3-diisocyano-1,3-butadiene in the form of a yellow solid. Yield: 69%.

NMR δ (CDCl₃): 3.94 (3H, s), 5.05 (2H, s), 4.9–6.2 (3H, m), 7.05 (6H, m) and 7.70 (4H, d).

Mass M/Z: 342.

EXAMPLE 11

The compound No. 4 obtained in Example 4 was ground with a pin mill so as to give a particle size of approximately 10 μm. 300 mg of the particles thus obtained were filled in an injection vial. Separately, 5 mg of Tween 80 and 10 mg of official purified gelatin were dissolved in 5 ml of distilled water for injection. To the compound No. 4 filled in the injection vial, was added the solution thus prepared upon use. After thoroughly mixing, the obtained suspension was intramuscularly administered.

EXAMPLE 12

Cytotoxicity of xanthocillin X monomethyl ether derivative

The cytotoxic effect of each compound of the present invention in vitro was evaluated in the following manner. Dulbecco's modified MEM medium containing 10% (v/v) of fetal calf serum was used as a medium while Meth-A solid tumor was used as a tumor. The cytotoxic effect of each compound on this tumor was examined. Meth-A cells, which had been subcultured in a carbon dioxide gas incubator, were suspended in the above-mentioned medium so as to give a density of 5×10⁴ cells/ml. 135 μl portions of the suspension thus obtained were poured into 96-well microtiter plates. Each test compound was dissolved in a small amount of DMF and diluted with Dulbecco's modified MEM medium to a predetermined concentration. 15 μl portions of test compound solutions at various concentrations were added thereto and then incubated in a carbon dioxide gas incubator for 3 days. After the completion of the incubation, the 50% inhibition concentration (IC₅₀) was determined by the MTT assay method ["Igaku no Ayumi", vol. 128, 733–735 (1984)].

Table 1 shows the results. As Table 1 indicates, the xanthocillin X monomethyl ether derivatives of the present invention show cytotoxic activities on the Meth-A cells.

TABLE 1

| Compound | IC₅₀ (μg/ml) |
| --- | --- |
| No. 1 | 0.64 |
| No. 2 | 0.70 |
| No. 3 | 1.5 |
| No. 5 | 0.7 |
| No. 6 | 0.24 |
| No. 7 | 1.8 |
| No. 8 | 1.7 |
| No. 9 | 1.8 |

EXAMPLE 13

Inhibition of tumor growth by xanthocillin X monomethyl ether derivative

The inhibition of tumor growth by the compounds of the present invention in vivo were evaluated in the following manner. 10⁶ cells of Meth-A murine tumor cells were transplanted to the dorsal subcutaneous part of a female Balb/c mouse aged 6 weeks. On the next day of the transplantation, a test compound at each concentrations was intraperitoneally administered to the animal. The compound was suspended in a 1% solution of carboxymethyl cellulose (CMC) and thoroughly mixed ultrasonically. Alternately, it was thoroughly ground in a mortar and then suspended in a CMC solution. Thus a sample for injection was prepared. The test compound was administered once a day for 4 days continuously. To a control group, a 1% solution of CMC was administered once a day for 4 days continuously. Two weeks after the transplantation, the dorsal tumor was taken out and weighed to thereby determine the inhibition of tumor growth.

Table 2 shows the results. As Table 2 indicates, the xanthocillin X monomethyl ether derivatives of the present invention intensely inhibited the growth of the Meth-A solid tumor.

TABLE 2

| Experiment No. | Compound | Dose (mg/kg/day) | Tumor weight* (g) | Inhibition of tumor growth (%) |
| --- | --- | --- | --- | --- |
| 1 | No. 1 | 10 | 0.39 ± 0.08 | 67.5 |
|   | control | — | 1.20 ± 0.47 | 0 |
| 2 | No. 4 | 30 | 0.27 ± 0.20 | 71.9 |
|   | control | — | 0.96 ± 0.60 | 0 |
| 3 | No. 2 | 30 | 0.22 ± 0.04 | 67.6 |
|   | control | — | 0.68 ± 0.18 | 0 |
| 4 | No. 7 | 30 | 0.60 ± 0.20 | 68.4 |
|   | No. 8 | 30 | 1.40 ± 0.30 | 26.3 |
|   | No. 9 | 30 | 0.60 ± 0.50 | 68.4 |
|   | control | — | 1.90 ± 1.2 | 0 |

*Mean ± standard deviation.

EXAMPLE 14

Acute toxicity of xanthocillin X monomethyl ether derivative

Table 3 shows the acute toxicities of the compounds of the present invention which were intraperitoneally administered to female Balb/c mice aged 7 weeks. Each compound showed a low toxicity.

TABLE 3

| Compound | $LD_{50}$ (mg/kg) |
| --- | --- |
| No. 1 | 120 |
| No. 3 | >120 |
| No. 6 | >120 |
| No. 8 | >300 |
| No. 9 | >300 |

While the invention has been described in detail and with reference to specific examples thereof, it will be apparent to one skilled in the art that various changes and modifications can be made therein without departing from the spirit and scope thereof.

What is claimed is:

1. A xanthocillin X monomethyl ether derivative represented by the following formula (I):

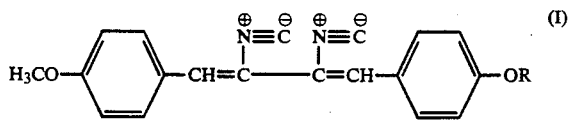

wherein R represents (a) a propenyl group (b) an ethoxycarbonyl group (c) a benzyl group, (d) an ethyl group substituted with a halogen atom, (e) a benzyl group substituted with a methyl group or a halogen atom, or (f) a benzoyl group.

2. The xanthocillin X monomethyl ether derivative as claimed in claim 1, wherein R represents a benzyl group.

3. An anti-solid tumor agent which contains a pharmaceutically effective amount of a xanthocillin X monomethyl ether derivative as claimed in claim 1 as an active ingredient, and a pharmaceutically acceptable carrier.

* * * * *